United States Patent
Shaw

(10) Patent No.: US 7,581,638 B2
(45) Date of Patent: Sep. 1, 2009

(54) TOOTHBRUSH SANITIZING CONTAINER

(76) Inventor: Louis P. Shaw, 5610 Chisolm Rd., Johns Island, SC (US) 29455

(*) Notice: Subject to any disclaimer, the term of this patent is extended or adjusted under 35 U.S.C. 154(b) by 267 days.

(21) Appl. No.: 11/704,833

(22) Filed: Feb. 8, 2007

(65) Prior Publication Data
US 2007/0187271 A1 Aug. 16, 2007

Related U.S. Application Data

(60) Provisional application No. 60/766,778, filed on Feb. 10, 2006.

(51) Int. Cl.
- B65D 81/24 (2006.01)
- B65D 83/10 (2006.01)
- B65D 69/00 (2006.01)
- A45D 44/18 (2006.01)

(52) U.S. Cl. ............... 206/209.1; 206/362; 206/362.1; 206/581; 132/308; 132/310

(58) Field of Classification Search ............ 206/209.1, 206/15.3, 362, 362.1, 362.2, 362.3, 581; 132/308–311
See application file for complete search history.

(56) References Cited

U.S. PATENT DOCUMENTS

| | | | | |
|---|---|---|---|---|
| 1,743,646 A | * | 1/1930 | Alderman, Jr. ............ 206/209.1 |
| 3,342,544 A | * | 9/1967 | Curiel ........................ 422/300 |
| D231,593 S | * | 5/1974 | Ockerman ................... D6/531 |
| 3,881,868 A | * | 5/1975 | Duke ........................ 206/209.1 |
| 4,121,600 A | * | 10/1978 | Riddick et al. .............. 132/310 |
| 4,214,657 A | | 7/1980 | Winston |
| 4,219,035 A | * | 8/1980 | Deconinck ................... 211/65 |
| 4,585,119 A | | 4/1986 | Boyington |
| 4,806,770 A | * | 2/1989 | Hylton et al. .......... 250/455.11 |
| 4,817,826 A | * | 4/1989 | Judge ......................... 222/192 |
| 4,915,219 A | | 4/1990 | Ottimo |
| 4,973,847 A | * | 11/1990 | Lackey et al. .......... 250/455.11 |
| 4,978,003 A | * | 12/1990 | Foster ........................ 206/217 |
| 4,995,509 A | | 2/1991 | Kornfeind |
| 4,995,511 A | * | 2/1991 | Evans ...................... 206/362.1 |
| 4,997,629 A | * | 3/1991 | Marchand et al. ........... 422/300 |
| 5,086,916 A | | 2/1992 | Gray |
| 5,107,987 A | | 4/1992 | Palazzolo et al. |
| 5,215,193 A | * | 6/1993 | Dennis ....................... 206/223 |
| 5,377,824 A | | 1/1995 | Seymour |
| 5,487,877 A | | 1/1996 | Choi |
| D370,812 S | * | 6/1996 | Simmonds ................... D6/531 |
| 5,522,497 A | * | 6/1996 | Stacy ...................... 206/209.1 |
| 5,566,823 A | * | 10/1996 | Summers ................. 206/209.1 |
| 5,662,130 A | * | 9/1997 | Wiltshire ................... 132/323 |
| 5,690,214 A | * | 11/1997 | Gaines et al. ............ 206/209.1 |
| 5,701,921 A | * | 12/1997 | Father et al. ................ 132/309 |

(Continued)

Primary Examiner—Ehud Gartenberg
Assistant Examiner—Jose S Stephens, III
(74) Attorney, Agent, or Firm—B. Craig Killough

(57) ABSTRACT

A container has an exterior wall and a interior wall that form a reservoir. A top or lid covers the reservoir. The top of lid has one or more orifices that receive a head of a toothbrush, which is immersed in a sanitizing agent contained in the reservoir. A second container engages the first container within a receptacle formed in the first container. The second container contains mouthwash. The close proximity of the toothbrush to the second container encourages the use of mouthwash at the time of brushing, and improves oral hygiene over brushing alone.

15 Claims, 2 Drawing Sheets

U.S. PATENT DOCUMENTS

| | | | |
|---|---|---|---|
| 5,865,195 A | 2/1999 | Carter | |
| 5,882,613 A | 3/1999 | Gipson, II | |
| 5,922,292 A | 7/1999 | Hecker et al. | |
| 5,960,801 A | 10/1999 | Vermooten et al. | |
| 6,099,813 A | 8/2000 | Gipson, II | |
| 6,119,854 A | 9/2000 | Prentice et al. | |
| 6,123,477 A | 9/2000 | Hecker | |
| 6,135,279 A * | 10/2000 | Dryer | 206/362.1 |
| 6,186,324 B1 * | 2/2001 | Catterson | 206/362.1 |
| 6,213,777 B1 * | 4/2001 | Seitzinger | 433/229 |
| 6,360,884 B1 * | 3/2002 | Smith et al. | 206/209.1 |
| 6,601,699 B1 * | 8/2003 | Naredo | 206/209.1 |
| 6,669,390 B1 | 12/2003 | Porter et al. | |
| 6,702,113 B2 | 3/2004 | Marino | |
| 6,769,828 B2 | 8/2004 | Clark | |
| 6,861,047 B1 | 3/2005 | Carnell | |
| 6,935,515 B1 * | 8/2005 | Sookoo | 211/65 |
| 2002/0031461 A1 | 3/2002 | Knipp | |
| 2002/0121449 A1 | 9/2002 | Bowie | |
| 2004/0025899 A1 * | 2/2004 | Pinsky | 132/310 |
| 2004/0050733 A1 * | 3/2004 | Page et al. | 206/362.2 |
| 2004/0134800 A1 | 7/2004 | Pigeon | |
| 2004/0211683 A1 | 10/2004 | Barham et al. | |
| 2005/0058583 A1 | 3/2005 | Goertz et al. | |
| 2005/0135870 A1 | 6/2005 | Frison | |
| 2005/0276736 A1 * | 12/2005 | Miller | 422/300 |
| 2006/0000729 A1 * | 1/2006 | Ceballos | 206/362.1 |
| 2006/0011209 A1 * | 1/2006 | Mehes et al. | 132/310 |

* cited by examiner

TOOTHBRUSH SANITIZING CONTAINER

CROSS-REFERENCE TO RELATED APPLICATIONS

The contents of Provisional Application Ser. No. 60/766,778 filed Feb. 10, 2006, on which the present application is based and benefit is claimed under 35 U.S.C. §119(e), is herein incorporated by reference.

FIELD OF THE INVENTION

This invention relates to toothbrush holders generally, and is more specifically directed to a device that sanitizes toothbrushes and encourages oral hygiene.

BACKGROUND OF THE INVENTION

A typical adult does not brush his or her teeth adequately, nor does the typical adult floss his or her teeth with the frequency recommended by dentists. Gingivitis is usually caused by bacterial plaque that accumulates in the spaces between the gums and the teeth and in calculus that forms on the teeth. The bacteria produce foreign chemicals and toxins that cause inflammation of the gums around the teeth. This inflammation can cause deep pockets between the teeth and gums and loss of bone around teeth otherwise known as periodontitis. Since the bone in the jaws holds the teeth into the jaws, the loss of bone may cause teeth to become loose, and eventually fall out. If the inflammation in the gums becomes especially well-developed, it can invade the gums and allow tiny amounts of bacteria and bacterial toxins to enter the bloodstream. Studies suggest this can result in a generalized increase in inflammation in the body cause possible long term heart problems. Periodontitis has also been linked to diabetes, arterosclerosis, osteoporosis and pre-term low birth weight babies. Bacteria and bacterial toxins are carried by tooth brushes, and brushing alone may cause the germs to remain in the mouth if the tooth brush is not sanitized between uses.

There is a need for a device that will hold and sanitize toothbrushes. The use of common antiseptic mouthwashes in combination with brushing, even if the brushing is otherwise inadequate, will kill harmful bacteria, and improve oral hygiene. The device should therefore encourage the use of mouthwash, and facilitate improved sanitation of toothbrushes.

SUMMARY OF THE INVENTION

The present invention is a container having an exterior wall and a interior wall that form a reservoir. A lid covers the reservoir. The lid has one or more orifices that receive a head of a toothbrush, which is immersed in a sanitizing agent contained in the reservoir. A second container engages the first container within a receptacle of the first container. The second container contains mouthwash. The close proximity of the toothbrush to the second container encourages the use of mouthwash at the time of brushing, and improves oral hygiene over brushing alone, particularly where the duration of brushing is inadequate.

DETAILED DESCRIPTION OF THE PREFERRED EMBODIMENT

Figure 1:
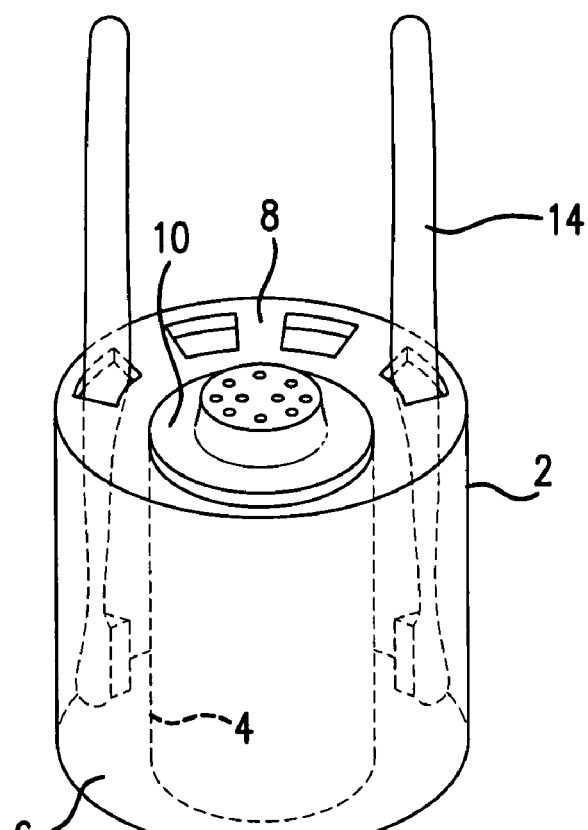
FIG. 1 is a perspective view of the toothbrush sanitizing container.
Figure 2:
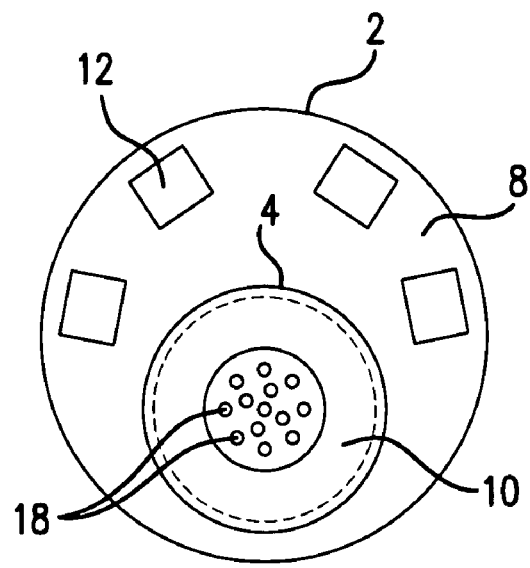
FIG. 2 is a top, plan view of the toothbrush sanitizing container.
Figure 3:
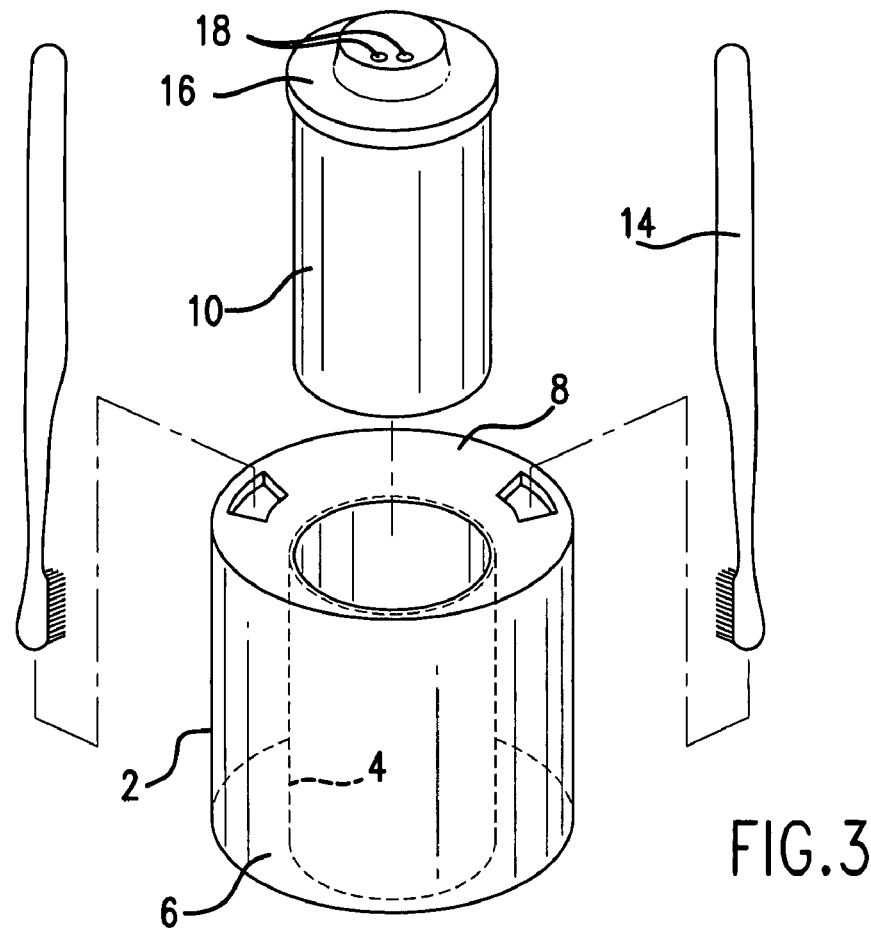
FIG. 3 is an exploded view of the toothbrush sanitizing container as shown in FIG. 1.

A first container is shown in the drawing figures. The first container has an exterior wall 2, an interior wall 4, a floor 6 and a lid 8. The interior wall forms a receptacle that receives a second container 10 therein. A second container is preferred to slidably engage the receptacle, and the second container is easily removable from the first container.

The first container, as shown in the embodiment of FIG. 1, is entirely enclosed, except for a plurality of orifices 12 in the lid. Each of the orifices is configured to receive a toothbrush 14, with the head of the toothbrush comprising the bristles of the toothbrush inserted to the lower region of the first container. The opposite end of the toothbrush, and a portion of the handle of the toothbrush is above the lid, as shown in FIG. 1. In a preferred embodiment, the lid comprises two-to-four orifices, but the exact number of orifices could depend upon the size of the device. It is preferred that the number of orifices be kept to a minimum, so that the sanitizing agent contained in the container has less exposure to contaminants that could enter the container through the orifices.

In one embodiment, and as shown in the drawing figures, the exterior wall 2 of the first container is annular, and more particularly, the exterior wall is round when viewed from above. The interior wall of the first container in this embodiment is also annular, and is also round, but the interior wall has a smaller radius than the exterior wall. In this embodiment, the interior wall does not engage or contact the first wall, so that the resulting reservoir formed between the exterior wall and in the interior wall is annular.

The second container 10 is a cup. The second container has a top or lid 16 on it, so that contaminants are inhibited from entering the container. The lid has a plurality of orifices 18 through which mouthwash passes to the user when the second container is used to transport mouthwash from the container to the mouth of the user. It is preferred that the second container have no more than two (2) or three (3) orifices to minimize the potential for contaminants to pass through the orifices. The orifices may have a valve so as to further inhibit contaminants entering the container. The valve may be actuated either by fluid pressure against the valve, or by the user providing oral suction to open the valve.

Figure 4:
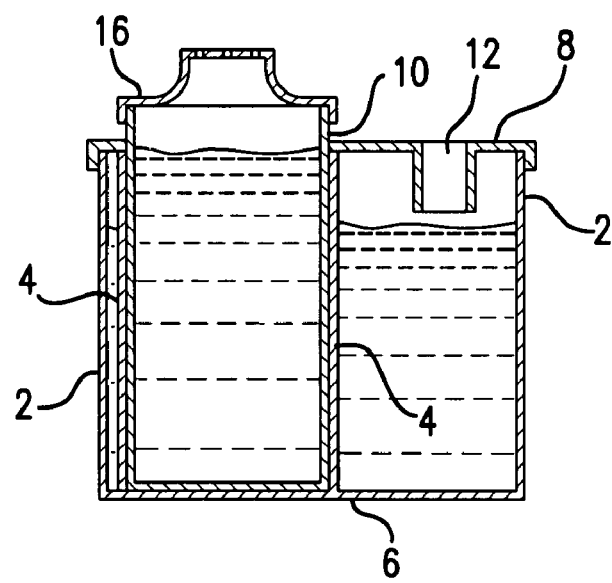
FIG. 4 is a sectioned view of the toothbrush sanitizing container.

In use, the first container is filled with a quantity of sanitizing agent. FIG. 4. The sanitizing agent may be mouthwash or similar germicide. The sanitizing agent should be a liquid antibacterial agent that is nontoxic, since a small quantity of the sanitizing agent may be placed in the user's mouth by means of the toothbrush. The level of the sanitizing agent in the first container should be sufficient to cover the bristles of the toothbrush. For most container configurations, it is not necessary to fill the first container to, or near, the top with mouthwash.

The second container is filled with mouthwash. It is preferred that the lid of the first container and the top 16 of the second container are removable from their respective containers, so that the sanitizing agent and mouthwash may be refilled and/or replaced as necessary. Particularly with regard to the sanitizing agent in the first container, it is recommended that the sanitizing agent be replaced from time-to-time so that the sanitizing agent is not contaminated, and that its efficacy is maintained.

At least one (1) toothbrush is inserted through the orifice of the lid of the first container. In one embodiment, each orifice is large enough to receive a head of the toothbrush, but is small enough to stop or prevent an enlarged portion of a handle of the toothbrush from passing through the orifice. The first container is of sufficient depth so that the head of the toothbrush approaches the floor of the first container, but is prohibited from reaching the floor of the container by the contact of the enlarged portion of the handle against the orifice. FIG. 1. The toothbrush is therefore suspended within the reservoir of the first container in this embodiment.

The sanitized toothbrush is removed from the first container through the orifice and used in a normal manner. The toothbrush is replaced into the first container after use.

The second container is lifted from the receptacle of the first container formed by the interior wall, and mouthwash is extracted from the second container by the user. The receptacle formed by the interior wall is eccentric relative to the exterior wall of the first container, to provide an enlarged area for receiving toothbrushes, while reducing the volume of sanitizing agent that is placed in the first container. After use, the second container is reinserted into and retained within the receptacle, so that second container is near the toothbrush, for convenience of use.

The first container is preferred to have a floor 6 that extends underneath the receptacle to limit travel of the second container within the receptacle. The interior of the first container does not communicate with the receptacle so that the sanitizing agent does not flow from the reservoir, formed by the exterior and interior walls of the first container, into the receptacle of the first container.

The reservoir is annular when viewed from the top as shown in the drawings. The device may be configured so that the reservoir is not annular. The device could be configured so that the receptacle is concentric with the exterior wall, rather than being eccentric as shown in the drawing figures. Other modifications could be made to the device while accomplishing the goals of the invention.

What is claimed is:

1. A toothbrush sanitizing container, comprising
   a) a first container comprising a generally vertical exterior wall and a generally vertical interior wall, wherein a reservoir is formed between said generally vertical exterior wall and said generally vertical interior wall, wherein a liquid antibacterial agent is present within the reservoir of the first container, and a second container receptacle is formed by the generally vertical interior wall of the first container and said receptacle is opposite said reservoir;
   b) the second container engages said first container and is retained within said first container and within the receptacle of said first container formed by said generally vertical interior wall of said first container, wherein said second container comprises a first opening in an upper portion of said container, and wherein second container comprises a removable top that covers said first opening of said second container, wherein said top comprises an orifice therein that allows a liquid antibacterial agent that is present in said second container to flow through the orifice of the top as a user drinks from said second container;
   c) a lid that covers a top opening of said first container that is between said generally vertical exterior wall and said generally vertical interior wall, said lid comprising plurality of orifices therein that are each configured to receive a head of a toothbrush, wherein each of the plurality of orifices allows one toothbrush head to pass into the reservoir of the first container, wherein each of a plurality of toothbrush heads is covered by the liquid antibacterial agent present within the reservoir, wherein the reservoir permits communication and flow of the liquid antibacterial agent within the reservoir so that the liquid antibacterial agent contacts each of the toothbrush heads present in the reservoir.

2. A toothbrush sanitizing container as described in claim 1, wherein said receptacle of said first container is open at top thereof.

3. A toothbrush sanitizing container as described in claim 1, wherein said receptacle of said first container is open at top thereof, and is enclosed at a bottom thereof by a floor of said first container.

4. A toothbrush sanitizing container as described in claim 1, wherein said receptacle of said first container does not communicate with said reservoir of said first container and said liquid antibacterial agent does not flow from said reservoir to said receptacle.

5. A toothbrush sanitizing container as described in claim 1, wherein said reservoir is annular, and said receptacle is within an interior of said annular reservoir.

6. A toothbrush sanitizing container as described in claim 1, wherein said plurality of orifices of said lid of said first container are configured to allow the plurality of toothbrush heads to pass there through, but wherein said plurality of orifices do not permit an enlarged portion of a handle attached to said plurality of toothbrush heads to pass through said orifice.

7. A toothbrush sanitizing container as described in claim 1, said plurality of orifices of said lid of said first container are configured to allow the plurality of toothbrush heads to pass there through, but wherein said plurality of orifices do not permit an enlarged portion of a handle attached to said plurality of toothbrush heads to pass through said orifice, and wherein said plurality of toothbrush heads are submerged in said liquid antibacterial agent in said reservoir, but said plurality of toothbrush heads do not contact a floor of said reservoir.

8. A toothbrush sanitizing container as described in claim 1, wherein said second container slidably engages said receptacle of said first container formed by said generally vertical interior wall of said first container.

9. A toothbrush sanitizing container as described in claim 1, wherein said second container has a plurality of orifices in said removable top.

10. A toothbrush sanitizing container as described in claim 1, wherein said second container is a cup that is not attached to said first container.

11. A toothbrush sanitizing container as described in claim 1, wherein said interior wall of said first container is positioned eccentrically relative to the exterior wall of said first container.

12. A toothbrush sanitizing container as described in claim 1, wherein the interior wall of the first container is annular and round and the receptacle formed by the interior wall of the first container is annular and round to receive and hold the second container, wherein the second container comprises an annular and round wall that engages the receptacle, and wherein the second container slidably engages the interior wall that forms the receptacle.

13. A toothbrush sanitizing container as described in claim 1, wherein the lid that covers the top opening of said first container forms a top opening for the receptacle, and the lid does not cover or obstruct the second container as the second container is removed from and placed into the receptacle by slidable engagement of the second container with the interior wall of the first container that forms the receptacle.

14. A toothbrush sanitizing container as described in claim 1, wherein the orifice of the removable top that covers said first opening of said second container has a valve therein.

15. A toothbrush sanitizing container as described in claim 1, wherein the plurality of orifices in the lid that covers the top opening of said first container are open and do not impede placement of said plurality of toothbrush heads into said reservoir.

* * * * *